United States Patent [19]

Shih et al.

[11] Patent Number: 4,882,334
[45] Date of Patent: Nov. 21, 1989

[54] N-(5,6,7,8-TETRAHYDROPYRIDO]2,3-D]PYRIMIDIN-6-YLETHL-THINEYL-AND FURYLCARBONYL)-GLUTAMIC ACID DERIVATIVES

[75] Inventors: Chuan Shih, Indianapolis, Ind.; Edward C. Taylor, Princeton, N.J.

[73] Assignees: The Trustees of Princeton University, Princeton, N.J.; Eli Lilly and Company, Indianapolis, Ind.

[21] Appl. No.: 198,207
[22] Filed: May 25, 1988
[51] Int. Cl.$^4$ .................. A61K 31/505; C07D 475/08
[52] U.S. Cl. .................................... 514/258; 544/279
[58] Field of Search ........................ 544/279; 514/258
[56] References Cited

U.S. PATENT DOCUMENTS 4,684,653 8/1987 Taylor et al. ...................... 544/279

*Primary Examiner*—Mukund J. Shah
*Assistant Examiner*—C. L. Cseh
*Attorney, Agent, or Firm*—Mathews, Woodbridge, Goebel, Pugh & Collins

[57] ABSTRACT

N-(Thienylcarbonyl)glutamic acid and N-(furylcarbonyl)glutamic acid derivatives in which the thienyl or furyl group is substituted with the 2-amino-4-hydroxy-5,6,7,8-tetrahydropyrido[2,3-d]pyrimidin-6-ylethyl or 2,4-diamino-5,6,7,8-tetrahydropyrido[2,3-d]-pyrimidin-6-ylethyl group are antineoplastic agents. Typical embodiments are N-[5-(2-{2-amino-4-hydroxy-5,6,7,8-tetrahydropyrido[2,3-d]pyrimidin-6-yl}ethyl)thien-2-ylcarbonyl]-L-glutamic acid and N-[5-(2-{2-amino-4-hydroxy-5,6,7,8-tetrahydropyrido[2,3-d]pyrimidin-6-yl}ethyl)fur-2-ylcarbony]-L-glutamic acid.

9 Claims, No Drawings

N-(5,6,7,8-TETRAHYDROPYRIDO]2,3-D]PYRIMI-DIN-6-YLETHL-THINEYL-AND FURYLCARBONYL)-GLUTAMIC ACID DERIVATIVES

The present invention pertains to the individual diastereomers and to the diastereomeric mixture of glutamic acid derivatives of the formula:

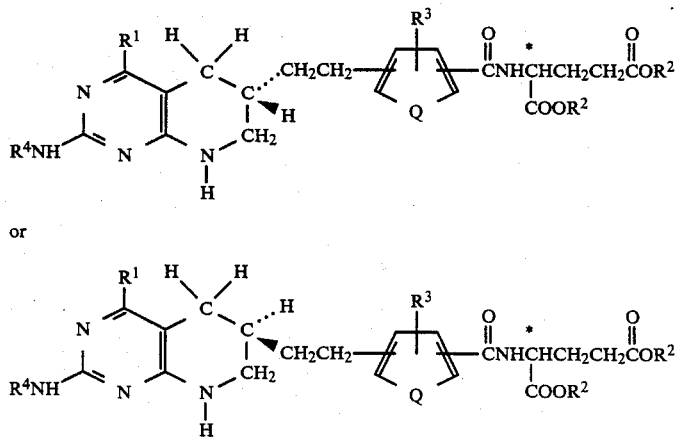

or in which:
- Q is —O— or —S—;
- $R^1$ is —OH or —NH$_2$;
- $R^2$ is hydrogen or a carboxy protecting group;
- $R^3$ is hydrogen, chloro, or fluoro;
- $R^4$ is hydrogen or an amino protecting group; and the configuration about the carbon atom designated * is S.

The compounds of Formula IA and IB have an inhibitory effect on one or more enzymes which utilize folic acid, and in particular metabolic derivatives of folic acid, as a substrate. The compounds thus can be used, alone or in combination, to inhibit the growth of those neoplasms which otherwise depend upon the enzymes so inhibited.

The invention also pertains to the pharmaceutically acceptable salts of the compounds of Formula IA and IB, to processes for the preparation of these compounds and their salts, to a method of combatting neoplastic growth in a mammal, and to pharmaceutical compositions containing these compounds or their salts.

The protecting groups designated by $R^2$ and $R^4$ and utilized herein denote groups which generally are not found in the final therapeutic compounds but which are intentionally introduced during a portion of the synthesis to protect a group which otherwise might react in the course of chemical manipulations, thereafter being removed at a later stage of the synthesis. Since compounds bearing such protecting groups thus are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974.

A carboxy group can be protected as an ester group which is selectively removable under sufficiently mild conditions not to disrupt the desired structure of the molecule, especially a lower alkyl ester such as methyl or ethyl and particularly one which is branched at the 1-position such as t.-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group can also be protected in the form of an organic silyl group such as tri-lower alkylsilyl, as for example trimethylsilyloxycarbonyl.

Amino groups similarly can be protected as an amide utilizing an acyl group which is selectively removable under mild conditions, especially formyl, a lower alkanoyl group which is branched at the 1-position, particularly tertiary alkanoyl such as pivaloyl, or a lower alkanoyl group which is substituted in the 1-position, as for example trifluoroacetyl.

Preferred compounds are those wherein $R^1$ is —OH and each of $R^2$ and $R^4$ is hydrogen. Also preferred are those compounds in which Q is —S—. Thus preferred species include the (R,S) and (S,S) diastereomers of N-[5-(2-{2-amino-4-hydroxy-5,6,7,8-tetrahydropyrido[2,3-d]pyrimidin-6-yl}ethyl)thien-2-ylcarbonyl]-L-glutamic acid; N-[5-(4-{2-amino-4-hydroxy-5,6,7,8-tetrahydropyrido[2,3-d]pyrimidin-6-yl}ethyl)-thien-2-ylcarbonyl]-L-glutamic acid; N-[5-(2-{2-amino-4-hydroxy-5,6,7,8-tetrahydropyrido[2,3-d]pyrimidin-6-yl}ethyl)thien-3-ylcarbonyl]-L-glutamic acid; N-[4-(2-{2-amino-4-hydroxy-5,6,7,8-tetrahydropyrido[2,3-d]pyrimidin-6-yl}ethyl)thien-3-ylcarbonyl]-L-glutamic acid; N-[3-(2-{2-amino-4-hydroxy-5,6,7,8-tetrahydropyrido[2,3-d]pyrimidin-6-yl}ethyl)thien-2-ylcarbonyl-L-glutamic acid; N-[2-(2-{2-amino-4-hydroxy-5,6,7,8-tetrahydropyrido[2,3-d]pyrimidin-6-yl}ethyl)-thien-3-ylcarbonyl]-L-glutamic acid; and N-[5-(2-{2- amino-4-hydroxy-5,6,7,8-tetrahydropyrido[2,3-d]pyrimidin-2-yl}ethyl)fur-2-ylcarbonyl-L-glutamic acid.

The compounds of the present invention often can be employed advantageously in the form of a pharmaceutically acceptable salt. Such forms, including hydrates thereof, are often crystalline and advantageous for forming solutions or formulating pharmaceutical compositions. Pharmaceutically acceptable salts with bases include those formed from the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts. The mono and disodium salts, particularly the disodium salt, are advantageous.

The compounds of this invention can be prepared through catalytic hydrogenation of a compound of the formula:

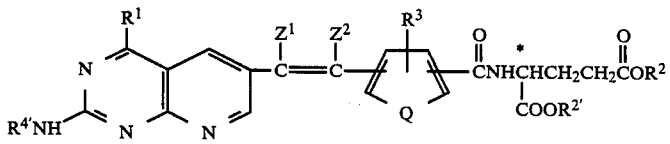

in which:
$Z^1$ and $Z^2$ taken individually are each hydrogen or taken together are a carbon-carbon bond;
$R^1$ and $R^3$ are as herein defined;
$R^{2'}$ is a carboxy protecting group; and
$R^{4'}$ is an amino protecting group.

Suitable hydrogenation catalysts include noble metals and noble metal oxides such as palladium or platinum oxide, rhodium oxide, and the foregoing on a support such as carbon or calcium oxide.

There is obtained a mixture of diastereomers of Formulas IA and IB in which $R^{2'}$ is a carboxy protecting group, and $R^{4'}$ is an amino protecting group. These protecting groups can then be removed through acidic or basic hydrolysis, as for example with sodium hydroxide, to yield the compounds of Formula I in which each of $R^2$ and $R^4$ is hydrogen.

Compounds of Formula II can be prepared utilizing procedures analogous to those described in European Patent Application No. 87308921.3. Thus an unsaturated compound of the formula:

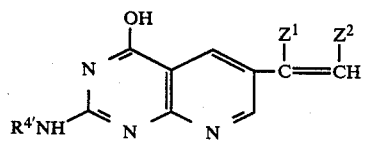

in which $Z^1$, $Z^2$, and $R^{4'}$ are as herein defined, is allowed to react with compound of the formula:

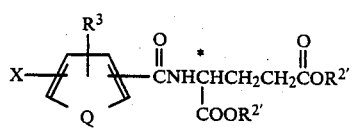

in which X is bromo or iodo and $R^{2'}$, $R^3$, and Q are as herein defined, in the presence of a palladium/trisubstituted phosphine catalyst of the type described by Sakamoto, *Synthesis*, 1983, 312 et seq.

There is thus obtained a compound of Formula II in which $R^1$ is —OH. When a compound in which $R^1$ is —NH$_2$ is desired, this product can be treated with 1,2,4-triazole and (4-chlorophenyl)dichlorophosphate and the product of this reaction then treated with concentrated ammonia.

Compounds of Formula IV are prepared by coupling a compound of the formula:

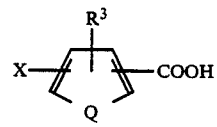

in which X, $R^3$, and Q are as herein defined, with a protected glutamic acid derivative of the formula:

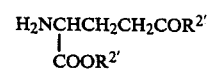

in which $R^{2'}$ is a carboxy protecting group, in the manner generally described in PCT application WO 86/05181, utilizing conventional condensation techniques for forming peptide bonds, such as activation of the carboxy group through formation of a mixed anhydride or acid chloride, treatment with DCC, or use of diphenyl-chlorophosphonate.

The mixture of the individual diastereomers depicted by Formulas IA and IB can be used therapeutically as such or can be separated mechanically as by chromatography. Alternatively, the individual diastereomers can be separated by forming diastereomeric salts with a chiral acid such as the individual enantiomers, of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the individual diastereomeric bases, optionally repeating the process, so as to obtain either or both substantially free of the other; i.e., in a form having an optical purity of >95%. This separation can be effected before or after removal of any protecting groups.

As noted, the compounds of this invention have an effect on one or more enzymes which utilize folic acid, and in particular metabolic derivatives of folic acid, as a substrate. The compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides and psoriasis.

The compounds can be administered orally but preferably are administered parenterally, alone or in combination with other therapeutic agents including other anti-neoplastic agents, steroids, etc., to a mammal suffering from neoplasm and in need of treatment. Parenteral routes of administration include intramuscular, intrathecal, intravenous and intra-arterial. Dosage regimens must be titrated to the particular neoplasm, the condition of the patient, and the response but generally doses will be from about 10 to about 100 mg/day for 5–10 days or single daily administration of 250–500 mg, repeated periodically; e.g. every 14 days. While having a low toxicity as compared to other antimetabolites now in use, a toxic response often can be eliminated by either or both of reducing the daily dosage or administering the compound on alternative days or at longer intervals such as every three days. Oral dosage forms include tablets and capsules containing from 1–10 mg of drug per unit dosage. Isotonic saline solutions containing 20–100 mg/ml can be used for parenteral administration.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

Dimethyl N-[5-(2-{2-Pivaloylamino-4-hydroxypyrido[2,3-d]pyrimidin-6-yl}ethynyl)thien-2ylcarbonyl]-L-glutamate A. A solution of 1.50 g. (7.25 mmol.) of 5-bromo-2-thiophenecarboxylic acid, several drops of dimethylformamide, and 2.21 mL. of thionyl chloride was heated at reflux for 2.5 hours. The solvent was removed under reduced pressure and the residue redissolved in 10 mL. of dry methylene chloride. This solution was added dropwise to an ice-cooled solution of 1.62 g. of dimethyl L-glutamate hydrochloride, 10 mg. of dimethylaminopyridine, and 2.11 mL. of triethylamine in 25 mL. of dry methylene chloride. When the addition was complete, the mixture was stirring at ambient temperatures for 12 hours and then diluted with water and extracted with methylene chloride. The organic extracts were washed with 1.0N hydrochloric acid and saturated sodium bicarbonate solution and then evaporated to yield 2.71 g. (100%) of dimethyl N-[5-bromothien-2-ylcarbonyl]-L-glutamate as a viscous oil which can be used in the following procedure without further purification.

Dimethyl N-[5-bromofur-2-ylcarbonyl]-L-glutamate, also a viscous oil, is prepared analogously from 5-bromo-2-furancarboxylic acid.

Dimethyl N-(5-bromothien-3-ylcarbonyl)-L-glutamate can be prepared in a similar fashion from 5-bromo-3-thienylcarboxylic acid.

B. A mixture of 1.70 g. (6.32 mmol.) of 2-pivaloylamino-4-hydroxy-6-ethynylpyrido[2,3-d]pyrimidine, 2.30 g. (6.32 mmol.) of dimethyl N-(5-bromothien-2-ylcarbonyl)-L-glutamate, 44 mg. of palladium chloride, 130 mg. of triphenylphosphine, 25 mg. of cuprous iodide, and 1.13 mL. of triethylamine in 30 mL. of acetonitrile was heated at reflux for 3 hours and then cooled to ambient temperature. The solvent was removed under reduced pressure and the residue column chromatographed (Waters 500) eluting with 1:19 methanol:methylene chloride to yield dimethyl N-[5-(2-{2-pivaloylamino-4-hydroxypyrido[2,3-d]pyrimidin-6yl}ethynyl)thien-2ylcarbonyl]-L-glutamate, m.p. 228°–230° C. Anal. Calc. for $C_{26}H_{27}N_5O_7S$: C, 56.41; H, 4.92; N, 12.65; S, 5.79. Found: C, 56.64; H, 4.77; N, 12.88; S, 5.58.

In as similar fashion by substituting an equivalent amount of dimethyl N-(5-bromofur-2-ylcarbonyl)-L-glutamate for dimethyl N-(5-bromothien-2-ylcarbonyl)-L-glutamate in the foregoing procedure, there can be obtained dimethyl N-[5-(2-pivaloylamino-4-hydroxypyrido[2,3-d]pyrimidin-6-yl}ethynyl)fur-2ylcarbonyl]-L-glutamate. In a representative experiment, the following physical constants were obtained for this compound: m.p. 135° C. (darkens), 181° C. (decomposition). Anal. Calc. for $C_{26}H_{25}N_5O_8$: C, 58.32; H, 4.71; N, 13.08. Found: C, 58.58; H, 4.92; N, 13.11.

Likewise by substituting an equivalent amount of dimethyl N-(5-bromothien-3-ylcarbonyl)-L-glutamate for dimethyl N-(5-bromothien-2-ylcarbonyl)-L-glutamate in the foregoing procedure, there can be obtained dimethyl N-[5-(2-{2-pivaloylamino-4-hydroxypyrido[2,3-d]pyrimidin-6-yl}ethynyl)thien-3-ylcarbonyl]-L-glutamate.

EXAMPLE 2

Dimethyl N-[5-(2-{2-Pivaloylamino-4-hydroxy-5,6,7,8-tetrahydropyrido[2,3-d]pyrimidin-6-yl}ethyl)thien-2-ylcarbonyl]-L-glutamate To a solution of 0.5 g. of dimethyl N-[5-(2-pivaloylamino-4-hydroxypyrido[2,3-d]pyrimidin-6-yl}ethynyl)thien-2ylcarbonyl]-L-glutamate in 30 mL. of glacial acetic acid were added 1.5 g. of 5% palladium on carbon. The mixture was hydrogenated under one atmosphere pressure with agitation for 18 hours, the catalyst removed by filtration, and the filtrate concentrated under reduced pressure. Chromatography on silica gel eluting with 1:19 methanol:chloroform yielded 100 mg. (19.7%) of dimethyl N-[5-(2-{2-pivaloylamino-4-hydroxypyrido[2,3-d]pyrimidin-6-yl}ethyl)thien-2-ylcarbonyl]-L-glutamate, and 204 mg. (40.2%) of the desired dimethyl N-[5-(2-{2-pivaloylamino-4-hydroxy-5,6,7,8-tetrahydropyrido[2,3-d]pyrimidin-6-yl}ethyl)-thien-2-ylcarbonyl]-L-glutamate, m.p. 152°–160° C. Anal. Calc. for $C_{26}H_{35}N_5O_7S$: C, 55.60; H, 6.28; N, 12.47. Found: C, 55.76; H, 6.23; N, 12.26. The partially hydrogenated by-product can be rehydrogenated to yield additional final product.

Similarly prepared from dimethyl N-[5-(2-{2-pivaloylamino-4-hydroxypyrido[2,3-d]pyrimidin-6-yl}ethynyl)fur-2ylcarbonyl]-L-glutamate is dimethyl N-[5-(2-}2-pivaloylamino-4-hydroxy-5,6,7,8-tetrahydropyrido[2,3-d]pyrimidin-6-yl}ethyl)fur-2-ylcarbonyl]-L-glutamate. In a representative experiment, the following physical contents were obtained for this compound: m.p. 155°–162° C.; Anal. Calc. for $C_{26}H_{33}N_5O_8$: C, 57.45; H, 6.12; N, 12.88. Found: C, 57.22; H, 6.08; N, 12.66.

Likewise dimethyl N-[5-(2-{2-pivaloylamino-4-hydroxy-5,6,7,8-tetrahydropyrido[2,3-d]pyrimidin-6-yl}ethyl)thien-3-ylcarbonyl]-L-glutamate can be prepared from dimethyl N-[5-(2-pivaloylamino-4-hydroxypyrido[2,3-d]pyrimidin-6-yl}ethynyl)thien-3-ylcarbonyl]-L-glutamate.

EXAMPLE 3

N-[5-(2-{2-Amino-4-hydroxy-5,6,7,8-tetrahydropyrido[2,3-d]pyrimidin-6-yl}ethyl)thien-2-ylcarbonyl]-L-glutamic Acid A solution of 100 mg. of dimethyl N-[5-(2-{2-pivaloylamino-4-hydroxy-5,6,7,8-tetrahydropyrido[2,3-d]pyrimidin-6-yl}ethyl)thien-2-ylcarbonyl]-L-glutamate in 15 mL. of 1.0N aqueous sodium hydroxide is stirred at room temperature for 120 hours and the pH then adjusted to 7.0 through the careful addition of 5.0N hydrochloric acid. The solid which formed was collected by filtration and dried at 80° C. to yield 61.5 mg (76.8%) of N-[5-(2-{2-amino-4-hydroxy-5,6,7,8-tetrahydropyrido[2,3-d]pyrimidin-6-yl}ethyl)thien-2-ylcarbonyl]-L-glutamic acid, m.p. 226°–240° C. (foaming and decomposition). NMR (DMSO-$d_6$ 300 MHz) delta: 9.80 (s, br, 1H), 8.45 (d, J=9 Hz, 1H), 7.62 (d, J=3 Hz, 1H), 6.87 (d, J=3 Hz, 1H), 6.30 (s, 1H), 6.04 (s, 2H), 4.28 (m, 1H), 3.12 (m, 1H), 2.84 (m, 3H), 2.36 (m, 1H), 2.02 (m, 1H), 1.83 (m, 2H), 1.57 (m, 3H).

Similarly prepared from dimethyl N-[5-(2-{2-pivaloylamino-4-hydroxy-5,6,7,8-tetrahydropyrido[2,3-d]pyrimidin-6-yl}ethyl)fur-2-ylcarbonyl]-L-glutamate is N-[5-(2-{2-amino-4-hydroxy-5,6,7,8-tetrahydropyrido[2,3-d]pyrimidin-6-yl}ethyl)fur-2-ylcarbonyl]-L-glutamic acid. In a representative experiment, the following physical constants were obtained for this compound: m.p. 204°–230° C. (foaming). NMR (DMSO-$d_6$ 300 MHz) delta: 9.80 (s, br, 1H), 8.27 (d, J=9 Hz, 1H), 7.03 (d, J=4 Hz, 1H), 6.30 (s, 1H), 6.25 (d, J=4 Hz, 1H), 6.04 (s, 2H), 4.30 (m, 1H), 3.16 (m, 1H), 2.65 (m, 3H), 2.42 (m, 1H), 2.16 (t, J=7 Hz, 2H), 2.01 (m, 1H), 1.84 (m, 2H), 1.57 (m, 3H).

N-[5-(2-{2-Amino-4-hydroxy-5,6,7,8-tetrahydropyrido[2,3-d]pyrimidin-6-yl}ethyl)thien-3ylcarbonyl]-L-glutamic acid can be prepared similarly from dimethyl N-[5-(2-{2-pivaloylamino-4-hydroxy-5,6,7,8-tetrahydropyrido[2,3-d]pyrimidin-6-yl}ethyl)thien-3-ylcarbonyl]-L-glutamate.

EXAMPLE 4

The IC$_{50}$ in whole cell human leukemia cell lines, CCRF-CEM, of N-[5-(2-{2-amino-4-hydroxy-5,6,7,8-tetrahydropyrido[2,3-d]pyrimidin-6-yl}ethyl)thien-2-ylcarbonyl]-L-glutamic acid is 0.0015 ug/mL. The IC$_{50}$ of N-[5-(2-{2-amino-4-hydroxy-5,6,7,8-tetrahydropyrido[2,3-d]pyrimidin-6-yl}ethyl)fur-2-ylcarbonyl]-L-glutamic acid is 0.010 ug/mL. In in vivo evaluation against C3H mammary adenocarcinoma in the mouse, N-[5-(2-{2-amino-4-hydroxy-5,6,7,8-tetrahydropyrido[2,3-d]pyrimidin-6-yl}ethyl)fur-2-ylcarbonyl]-L-glutamic acid produced 89% inhibition at 100 mg/kg, 69% inhibition at 50 mg/kg, and 59% inhibition at 25 mg/kg.

Against 6C3HED Lymphosarcoma in the mouse, the following values were obtained for N-[5-(2-{2-amino-4-hydroxy-5,6,7,8-tetrahydropyrido[2,3-d]pyrimidin-6-yl}ethyl)thien-2-ylcarbonyl]-L-glutamic acid.

| Administration | Dose (mg/kg) | Inhibition | Survivors |
|---|---|---|---|
| I.P. (0.5 mL) Daily for 8 days | 25.00 | toxic | 0/10 |
|  | 12.5 | toxic | 0/10 |
|  | 6.25 | toxic | 0/10 |
|  | 3.12 | 100% | 4/10 |
|  | 1.56 | 100% | 10/10 |
|  | 0.78 | 93% | 10/10 |
| I.P. (0.5 mL) on days 1, 4 and 7 of 8 days | 100.00 | 100% | 2/10 |
|  | 50.00 | 100% | 7/10 |
|  | 25.00 | 100% | 10/10 |
|  | 12.00 | 100% | 10/10 |
| I.P. (0.5 mL) single dose on day 1 of 8 days | 400.00 | 100% | 4/10 |
|  | 200.00 | 99% | 8/10 |
|  | 100.00 | 94% | 9/10 |

What is claimed is:

1. A compound selected from the group consisting of a glutamic acid derivative having the formula:

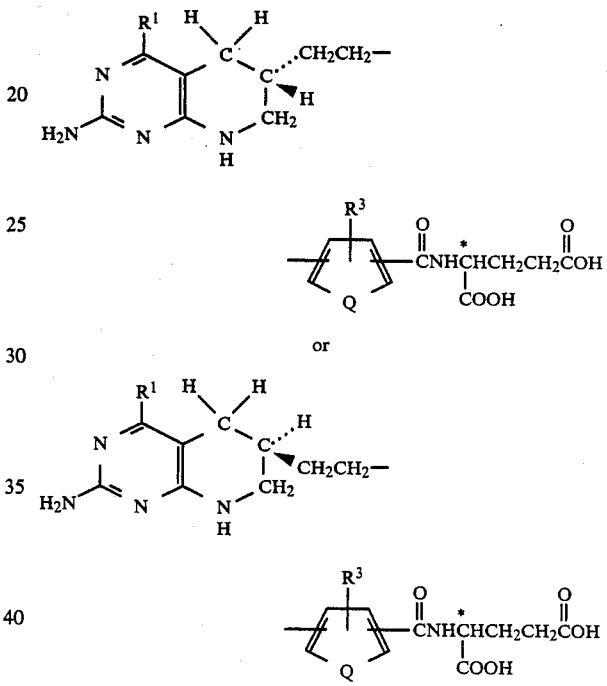

in which:

Q is —O— or —S—;
R$^1$ is —OH or —NH$_2$;
R$^3$ is hydrogen, chloro, or fluoro;
the configuration about the carbon atom designated * is S; and
the pharmaceutically acceptable salts thereof.

2. A compound according to claim 1 wherein R$^1$ is —OH.

3. A compound according to claim 2 wherein Q is —S—.

4. A compound according to claim 3 which is (S,S)-N-[5-(2-{2-amino-4-hydroxy-5,6,7,8-tetrahydropyrido[2,3-d]pyrimidin-6-yl}ethyl)thien-2-ylcarbonyl]-L-glutamic acid or (R,S)-N-[5-(2-{2-amino-4-hydroxy-5,6,7,8-tetrahydropyrido[2,3-d]pyrimidin-6-yl{ethyl)thien-2-ylcarbonyl]-L-glutamic acid.

5. A compound according to claim 2 wherein Q is —O—.

6. A compound according to claim 5 which is (S,S)-N-[5-(2-{2-amino-4-hydroxy-5,6,7,8-tetrahydropyrido[2,3-d]pyrimidin-6-yl}ethyl)fur-2-ylcarbonyl]-L-glutamic acid or (R,S)-N-[5-(2-{2-amino-4-hydroxy-5,6,7,8-tetrahydropyrido[2,3-d]pyrimidin-6-yl}ethyl)fur-2-ylcarbonyl]-L-glutamic acid.

7. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 1.

8. A pharmaceutical composition for inhibiting neoplastic growth in a mammal which growth is dependent on folic acid or a metabolic derivative of folic acid as a substrate, which comprises an amount of a compound according to claim 1 which upon administration to the mammal in a single or multiple dose regimen is effective to inhibit said growth, in combination with a pharmaceutically acceptable carrier.

9. A compound selected from the group consisting of a glutamic acid derivative having the formula:

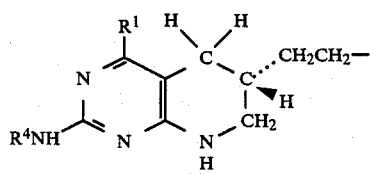

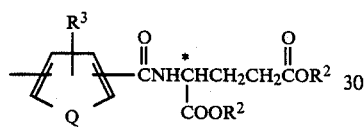

or

-continued

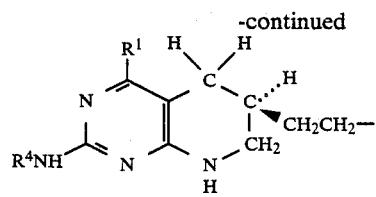

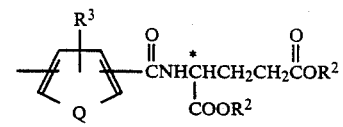

in which:

Q is —O— or —S—;

$R^1$ is —OH or —NH$_2$;

$R^2$ is hydrogen or a carboxy protecting group selected from the group consisting of (a) a straight or branched lower alkyl ester which is unsubstituted or substituted in the 1- or 2-position with (i) lower alkoxy, (ii) lower alkylthio, (iii) halogen, (iv) phenyl which is unsubstituted or mono-, di- or tri-substituted with lower alkyl, lower alkoxy, hydroxy, halo, or nitro, or (v) aroyl, or (b) a silyl group;

$R^3$ is hydrogen, chloro, or fluoro;

$R^4$ is hydrogen or an unsubstituted or substituted acyl amino protecting group;

at least one of $R^2$ and $R^4$ being other than hydrogen; and the configuration about the carbon atom designated * is S.

* * * * *